US010072058B2

(12) United States Patent
Wang et al.

(10) Patent No.: US 10,072,058 B2
(45) Date of Patent: Sep. 11, 2018

(54) CHIMERIC VIRUS-LIKE PARTICLES INCORPORATING FUSION GPI ANCHORED GM-CSF AND IL-4 CONJUGATES

(71) Applicants: Emory University, Atlanta, GA (US); Children's Healthcare of Atlanta, Inc., Atlanta, GA (US)

(72) Inventors: Baozhong Wang, Dultuh, GA (US); Richard W. Compans, Atlanta, GA (US); Jacques Galipeau, Atlanta, GA (US); Jiusheng Deng, Snellville, GA (US)

(73) Assignees: Emory University, Atlanta, GA (US); Children's Healthcare of Atlanta, Inc., Atlanta, GA (US)

( * ) Notice: Subject to any disclaimer, the term of this patent is extended or adjusted under 35 U.S.C. 154(b) by 0 days.

(21) Appl. No.: 15/142,169

(22) Filed: Apr. 29, 2016

(65) Prior Publication Data

US 2016/0318985 A1 Nov. 3, 2016

Related U.S. Application Data

(60) Provisional application No. 62/154,256, filed on Apr. 29, 2015.

(51) Int. Cl.

| | |
|---|---|
| ***C07K 14/54*** | (2006.01) |
| ***C07K 14/535*** | (2006.01) |
| ***C07K 14/005*** | (2006.01) |
| ***C12N 5/10*** | (2006.01) |
| ***C12N 15/63*** | (2006.01) |
| ***C12N 15/79*** | (2006.01) |
| ***C07K 14/705*** | (2006.01) |
| ***C07K 14/435*** | (2006.01) |
| ***A61K 39/12*** | (2006.01) |
| ***C07K 16/10*** | (2006.01) |
| *A61K 39/00* | (2006.01) |

(52) U.S. Cl.

CPC .......... *C07K 14/5406* (2013.01); *A61K 39/12* (2013.01); *C07K 14/005* (2013.01); *C07K 14/435* (2013.01); *C07K 14/535* (2013.01); *C07K 14/70596* (2013.01); *C07K 16/1063* (2013.01); *A61K 2039/5258* (2013.01); *A61K 2039/543* (2013.01); *A61K 2039/55522* (2013.01); *A61K 2039/55527* (2013.01); *A61K 2039/575* (2013.01); *C07K 2317/33* (2013.01); *C07K 2317/76* (2013.01); *C07K 2317/92* (2013.01); *C07K 2319/035* (2013.01); *C07K 2319/912* (2013.01); *C12N 15/63* (2013.01); *C12N 15/79* (2013.01); *C12N 2740/16023* (2013.01); *C12N 2740/16034* (2013.01); *C12N 2740/16122* (2013.01); *C12N 2740/16134* (2013.01); *C12N 2740/16222* (2013.01)

(58) Field of Classification Search

None

See application file for complete search history.

(56) References Cited

U.S. PATENT DOCUMENTS

| | | | |
|---|---|---|---|
| 2006/0216702 | A1 | 9/2006 | Compans |
| 2010/0196419 | A1 | 8/2010 | Compans |
| 2014/0255441 | A1 | 9/2014 | Compans |

FOREIGN PATENT DOCUMENTS

| | | |
|---|---|---|
| WO | 2014066443 | 5/2014 |

OTHER PUBLICATIONS

Wells, 1990, Biochemistry 29:8509-8517.*
Bork, 2000, Genome Research 10:398-400.*
Skolnick et al., 2000, Trends in Biotech. 18(1):34-39.*
Doerks et al., 1998, Trends in Genetics 14:248-250.*
Tokuriki and Tawflik, Current Opinion in Structural Biology 2009, 19: 596-604.*
Crystal R, Science, 1995. vol. 270, pp. 404-410.*
Juengst et al, British Medical Journal; 2003, vol. 326, pp. 1410-1411.*
Gabor M. Rubanyi , Mol Aspects Med , 2001 vol. 22, pp. 113-142.*
Dent et al, (Blood, 2012, vol. 120:1048).*
Jacques Galipeau, (Cliff Michaels, Licensing Associate, OTT Breakfast Club, May 21, 2013).*
Deng et al. Engineered Fusokine GIFT4 Licenses the Ability of B Cells to Trigger a Tumoricidal T-cell Response, Cancer Res; 74(15) 2014.
Hellerstein et al. Co-expression of HIV-1 virus-like particles and granulocyte-macrophage colony stimulating factor by GEO-D03 DNA vaccine, Human Vaccines & Immunotherapeutics 8:11, 1654-1658, 2012.
Hikino et al. Granulocyte/Macrophage Colony-stimulating Factor and Interleukin-4-induced Dendritic Cells, Anticancer Research 24: 1609-1616 (2004).
Lehner et al. Up-regulation of beta-chemokines and down-modulation of CCR5 co-receptors inhibit simian immunodeficiency virus transmissions in non-human primates, Immunology, 2000, 99, 569-577.
Pennati et al. Maltose-Binding Protein Fusion Allows for High Level Bacterial Expression and Purification of Bioactive Mammalian Cytokine Derivatives, PLoS ONE 9(9): e106724, 2014.

(Continued)

*Primary Examiner* — Bridget E Bunner
(74) *Attorney, Agent, or Firm* — Emory Patent Group

(57) ABSTRACT

This disclosure relates to a GM-CSF and IL-4 conjugate fused to a glycolipid (GPI)-anchoring sequence that is incorporated into chimeric virus-like particles (VLPs) enriched with a viral protein, e.g., viral envelope protein or HIV envelope protein. In certain embodiments, the disclosure relates to methods of immunization with the chimeric VLPs disclosed herein. In certain embodiments, the disclosure relates to methods of immunization with disclosed HIV antigen containing VLPs through an intramuscular priming-intranasal boosting immunization route.

16 Claims, 5 Drawing Sheets

Specification includes a Sequence Listing.

(56) References Cited

OTHER PUBLICATIONS

Skountzou et al. Incorporation of Glycosylphosphatidylinositol-Anchored Granulocyte-Macrophage Colony-Stimulating Factor or CD40 Ligand Enhances Immunogenicity of Chimeric Simian Immunodeficiency Virus-Like Particles, Journal of Virology, 2007, p. 1083-1094.

Wang et al. Cytokine Regulation of Human Immunodeficiency Virus Type 1 Entry and Replication in Human Monocytes/Macrophages through Modulation of CCR5 Expression, Journal of Virology, 1998, p. 7642-7647.

* cited by examiner

SEQUENCE LISTING

<160> NUMBER OF SEQ ID NOS: 7

<210> SEQ ID NO 1
<211> LENGTH: 142
<212> TYPE: PRT
<213> ORGANISM: Artificial sequence
<220> FEATURE:
<223> OTHER INFORMATION: Synthetic

<400> SEQUENCE: 1

```
Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
    50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Glu Thr Ser Cys Ala
            100                 105                 110

Thr Gln Thr Ile Thr Phe Glu Ser Phe Lys Glu Asn Leu Lys Asp Phe
        115                 120                 125

Leu Leu Val Ile Pro Phe Asp Cys Trp Glu Pro Val Gln Glu
    130                 135                 140
```

<210> SEQ ID NO 2
<211> LENGTH: 153
<212> TYPE: PRT
<213> ORGANISM: Artificial sequence
<220> FEATURE:
<223> OTHER INFORMATION: Synthetic

<400> SEQUENCE: 2

```
Met Gly Leu Thr Ser Gln Leu Leu Pro Pro Leu Phe Phe Leu Leu Ala
1               5                   10                  15

Cys Ala Gly Asn Phe Val His Gly His Lys Cys Asp Ile Thr Leu Gln
            20                  25                  30

Glu Ile Ile Lys Thr Leu Asn Ser Leu Thr Glu Gln Lys Thr Leu Cys
        35                  40                  45

Thr Glu Leu Thr Val Thr Asp Ile Phe Ala Ala Ser Lys Asn Thr Thr
    50                  55                  60

Glu Lys Glu Thr Phe Cys Arg Ala Ala Thr Val Leu Arg Gln Phe Tyr
65                  70                  75                  80

Ser His His Glu Lys Asp Thr Arg Cys Leu Gly Ala Thr Ala Gln Gln
                85                  90                  95

Phe His Arg His Lys Gln Leu Ile Arg Phe Leu Lys Arg Leu Asp Arg
            100                 105                 110

Asn Leu Trp Gly Leu Ala Gly Leu Asn Ser Cys Pro Val Lys Glu Ala
        115                 120                 125

Asn Gln Ser Thr Leu Glu Asn Phe Leu Glu Arg Leu Lys Thr Ile Met
    130                 135                 140

Arg Glu Lys Tyr Ser Lys Cys Ser Ser
145                 150
```

<210> SEQ ID NO 3
<211> LENGTH: 137
<212> TYPE: PRT
<213> ORGANISM: Artificial sequence
<220> FEATURE:
<223> OTHER INFORMATION: Synthetic

<400> SEQUENCE: 3

Met Gly Leu Thr Ser Gln Leu Leu Pro Pro Leu Phe Phe Leu Leu Ala
1 5 10 15

Cys Ala Gly Asn Phe Val His Gly His Lys Cys Asp Ile Thr Leu Gln
20 25 30

Glu Ile Ile Lys Thr Leu Asn Ser Leu Thr Glu Gln Lys Asn Thr Thr
35 40 45

Glu Lys Glu Thr Phe Cys Arg Ala Ala Thr Val Leu Arg Gln Phe Tyr
50 55 60

Ser His His Glu Lys Asp Thr Arg Cys Leu Gly Ala Thr Ala Gln Gln
65 70 75 80

Phe His Arg His Lys Gln Leu Ile Arg Phe Leu Lys Arg Leu Asp Arg
85 90 95

Asn Leu Trp Gly Leu Ala Gly Leu Asn Ser Cys Pro Val Lys Glu Ala
100 105 110

Asn Gln Ser Thr Leu Glu Asn Phe Leu Glu Arg Leu Lys Thr Ile Met
115 120 125

Arg Glu Lys Tyr Ser Lys Cys Ser Ser
130 135

<210> SEQ ID NO 4
<211> LENGTH: 29
<212> TYPE: PRT
<213> ORGANISM: Artificial sequence
<220> FEATURE:
<223> OTHER INFORMATION: Synthetic

<400> SEQUENCE: 4

Leu Ser Asn Gly Gly Thr Ser Leu Ser Glu Lys Thr Val Leu Leu Leu
1 5 10 15

Val Thr Pro Phe Leu Ala Ala Ala Trp Ser Leu His Pro
20 25

<210> SEQ ID NO 5
<211> LENGTH: 5
<212> TYPE: PRT
<213> ORGANISM: Artificial sequence
<220> FEATURE:
<223> OTHER INFORMATION: Synthetic

<400> SEQUENCE: 5

Gly Gly Gly Gly Ser
1 5

<210> SEQ ID NO 6
<211> LENGTH: 21
<212> TYPE: PRT
<213> ORGANISM: Artificial sequence
<220> FEATURE:
<223> OTHER INFORMATION: Synthetic

<400> SEQUENCE: 6

Met Lys Phe Leu Val Asn Val Ala Leu Val Phe Met Val Val Tyr Ile
1 5 10 15

```
Ser Tyr Ile Tyr Ala
            20


<210> SEQ ID NO 7
<211> LENGTH: 350
<212> TYPE: PRT
<213> ORGANISM: Artificial sequence
<220> FEATURE:
<223> OTHER INFORMATION: Synthetic

<400> SEQUENCE: 7

Met Lys Phe Leu Val Asn Val Ala Leu Val Phe Met Val Val Tyr Ile
1               5                   10                  15

Ser Tyr Ile Tyr Ala Met Trp Leu Gln Ser Leu Leu Leu Leu Gly Thr
            20                  25                  30

Val Ala Cys Ser Ile Ser Ala Pro Ala Arg Ser Pro Ser Pro Ser Thr
        35                  40                  45

Gln Pro Trp Glu His Val Asn Ala Ile Gln Glu Ala Arg Arg Leu Leu
    50                  55                  60

Asn Leu Ser Arg Asp Thr Ala Ala Glu Met Asn Glu Thr Val Glu Val
65                  70                  75                  80

Ile Ser Glu Met Phe Asp Leu Gln Glu Pro Thr Cys Leu Gln Thr Arg
                85                  90                  95

Leu Glu Leu Tyr Lys Gln Gly Leu Arg Gly Ser Leu Thr Lys Leu Lys
            100                 105                 110

Gly Pro Leu Thr Met Met Ala Ser His Tyr Lys Gln His Cys Pro Pro
        115                 120                 125

Glu Thr Ser Cys Ala Thr Gln Thr Ile Thr Phe Glu Ser Phe Lys Glu
    130                 135                 140

Asn Leu Lys Asp Phe Leu Leu Val Ile Pro Phe Asp Cys Trp Glu Pro
145                 150                 155                 160

Val Gln Glu Gly Gly Gly Gly Ser Met Gly Leu Thr Ser Gln Leu Leu
                165                 170                 175

Pro Pro Leu Phe Phe Leu Leu Ala Cys Ala Gly Asn Phe Val His Gly
            180                 185                 190

His Lys Cys Asp Ile Thr Leu Gln Glu Ile Ile Lys Thr Leu Asn Ser
        195                 200                 205

Leu Thr Glu Gln Lys Thr Leu Cys Thr Glu Leu Thr Val Thr Asp Ile
    210                 215                 220

Phe Ala Ala Ser Lys Asn Thr Thr Glu Lys Glu Thr Phe Cys Arg Ala
225                 230                 235                 240

Ala Thr Val Leu Arg Gln Phe Tyr Ser His His Glu Lys Asp Thr Arg
                245                 250                 255

Cys Leu Gly Ala Thr Ala Gln Gln Phe His Arg His Lys Gln Leu Ile
            260                 265                 270

Arg Phe Leu Lys Arg Leu Asp Arg Asn Leu Trp Gly Leu Ala Gly Leu
        275                 280                 285

Asn Ser Cys Pro Val Lys Glu Ala Asn Gln Ser Thr Leu Glu Asn Phe
    290                 295                 300

Leu Glu Arg Leu Lys Thr Ile Met Arg Glu Lys Tyr Ser Lys Cys Ser
305                 310                 315                 320

Ser Leu Ser Asn Gly Gly Thr Ser Leu Ser Glu Lys Thr Val Leu Leu
                325                 330                 335

Leu Val Thr Pro Phe Leu Ala Ala Ala Trp Ser Leu His Pro
            340                 345                 350
```

CHIMERIC VIRUS-LIKE PARTICLES INCORPORATING FUSION GPI ANCHORED GM-CSF AND IL-4 CONJUGATES

CROSS REFERENCE TO RELATED APPLICATIONS

This application claims the benefit of U.S. Provisional Application No. 62/154,256 filed Apr. 29, 2015. The entirety of this application is hereby incorporated by reference for all purposes.

STATEMENT REGARDING FEDERALLY SPONSORED RESEARCH OR DEVELOPMENT

This invention was made with government support under Grant R01AI101047 awarded by the National Institutes of Health. The government has certain rights in the invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy, and is hereby incorporated by reference into the specification. The name of the text file containing the Sequence Listing is 14216US_ST25.txt. The text file is 8 KB, was created on Apr. 29, 2016, and is being submitted electronically via EFS-Web.

BACKGROUND

Combination antiretroviral therapy (ART) has shown extraordinary success in reducing HIV transmission and prolonging life of subjects with HIV. However, in the vast majority of instances, ART does not entirely clear the virus, and may people continue to become newly infected. Thus, there is a need to identify an effective HIV vaccination method. Skountzou et al., report incorporation of glycosylphosphatidylinositol-anchored granulocyte-macrophage colony-stimulating factor or CD40 ligand enhances immunogenicity of chimeric simian immunodeficiency virus-like particles. J Virol, 2007, 81(3):1083-1094. See also Hellerstein et al. Hum Vaccin Immunother. 2012, 8(11):1654-8.

Interleukin 4 (IL-4) serves as a signal to activate and elicit antibody class switching by B lymphocytes and converts naive helper T lymphocytes to active T lymphocytes. U.S. Pat. No. 6,838,081 reports enhancing the development of antigen presenting cells from precursor cells by administering a combination of IL-4 and GM-CSF. See also, U.S. Patent Application 2004/0072299, and Hikino et al., Anticancer Res, 24: 1609-1616 (2004). GIFT fusokines are the fused proteins derived from granulocyte-macrophage colony-stimulating factor (GM-CSF) and cytokine transgenes. Deng et al. report a fusokine, GIFT4, generated by N-terminal coupling of GM-CSF to interleukin-4 (IL4). Cancer Res, 2014, 74:4133-4144. See also WO2014/066443.

References cited herein are not an admission of prior art.

SUMMARY

This disclosure relates to a GM-CSF and IL-4 conjugate fused to a glycolipid (GPI)-anchoring sequence that is incorporated into chimeric virus-like particles (VLPs) enriched with a viral protein, e.g., viral envelope protein or HIV envelope protein. In certain embodiments, the disclosure relates to methods of immunization with the chimeric VLPs disclosed herein. In certain embodiments, the disclosure relates to methods of immunization with disclosed HIV antigen containing VLPs through an intramuscular priming-intranasal boosting immunization route.

In certain embodiments, the disclosure relates to nucleic acids comprising a segment encoding a fusion protein comprising granulocyte-macrophage colony-stimulating factor and interleukin 4 and a glycosylphosphatidylinositol signal sequence. In certain embodiments, the granulocyte-macrophage colony-stimulating factor segment comprises MWLQSLLLLGTVACSISAPARSPSPSTQPWEHVNAIQEARRLLNLSRDTAAEMNETVEVI SEMFDLQEPTCLQTRLELYKQGLRGSLTKLKGPLTMMASHYKQHCPPETSCATQTITFE SFKENLKDFLLVIPFDCWEPVQE (SEQ ID NO: 1) or variants thereof with greater than 70% identity. In certain embodiments, the interleukin 4 segment comprises MGLTSQLLPPLFFLLACAGNFVHGHKCDITLQEIIKTLNSLTEQKTLCTELTVTDIFAASK NTTEKETFCRAATVLRQFYSHHEKDTRCLGATAQQFHRHKQLIRFLKRLDRNLWGLAG LNSCPVKEANQSTLENFLERLKTIMREKYSKCSS (SEQ ID NO: 2) or variants thereof with greater than 70% identity. In certain embodiments, the glycosylphosphatidylinositol signal sequence CD59 segment comprises LSNGGTSLSEKTVLLLVTPFLAAAWSLHP (SEQ ID NO: 5) or variants thereof with greater than 70% identity. Other glycosylphosphatidylinositol signal sequences are contemplated such as, the GPI anchor sequence of human LFA3, CD55, human Fcγ receptor III (CD16b). See Kueng et al., J Virol, 2007, 81(16):8666-8676.

In certain embodiments, the fusion protein further comprises a melittin signal peptide segment comprising MKFLVNVALVFMVVYISYIYA (SEQ ID NO: 6) or variants thereof with greater than 70% identity. In certain embodiments, the fusion protein segment comprises or consists essentially of MKFLVNVALVFMVVYISYIYAMWLQSLLLLGTVACSISAPARSPSPSTQPWEHVNAIQE ARRLLNLSRDTAAEMNETVEVISEMFDLQEPTCLQTRLELYKQGLRGSLTKLKGPLTMM ASHYKQHCPPETSCATQTITFESFKENLKDFLLVIPFDCWEPVQEGGGGSMGLTSQLLPP LFFLLACAGNFVHGHKCDITLQEIIKTLNSLTEQKTLCTELTVTDIFAASKNTTEKETFCR AATVLRQFYSHHEKDTRCLGATAQQFHRHKQLIRFLKRLDRNLWGLAGLNSCPVKEAN QSTLENFLERLKTIMREKYSKCSSLSNGGTSLSEKTVLLLVTPFLAAAWSLHP (SEQ ID NO: 7), or variants thereof with greater than 70% identity.

In certain embodiments, the disclosure relates to chimeric virus-like particle comprising the fusion protein disclosed herein. In certain embodiments, the disclosure relates to isolated fusion proteins encoded disclosed herein. In certain embodiments, the disclosure relates to vectors comprising the nucleic acids arranged as disclosed herein in operable combination with a promoter sequence. In certain embodiments, the chimeric virus-like particle further comprises a viral protein or envelope protein, e.g., HIV gp160, gp120, or gp41 or an influenza, hemagglutinin, HA1, A, B, C, and E antigenic epitopes on the HA1 subunit of the influenza virus hemagglutinin, neuraminidase, M2 protein, M2e protein, M1 protein, or combinations thereof.

In certain embodiments, the disclosure relates to methods of vaccination comprising administering an effective amount of the chimeric virus-like particle disclosed herein to a subject in need thereof. In certain embodiments, the disclosure relates to methods of treating or preventing a viral infection comprising administering an effective amount of the chimeric virus-like particle as disclosed herein to a subject in need thereof. In certain embodiments, the administration is intramuscular. In certain embodiments, a second administration is provided more than two weeks after an initial administration. In certain embodiments, the second administration is intranasal. In certain embodiments, the methods further comprise a third administration. In certain embodiments, the methods further comprise administration is in combination with the administration of another antiviral agent, antigen, adjuvant, or vaccine.

In certain embodiments, the disclosure relates to pharmaceutical or vaccine compositions comprising a chimeric virus-like particle comprising a GM-CSF and IL-4 conjugate fused to a glycolipid (GPI)-anchoring sequence that is incorporated into chimeric virus-like particles (VLPs) and alternative embodiments disclosed herein and a pharmaceutically acceptable excipient.

In certain embodiments, a vaccine composition comprises a chimeric virus-like particle comprising GM-CSF and IL-4 conjugate fused to a glycolipid (GPI)-anchoring sequence that is incorporated into chimeric virus-like particles (VLPs) and an antigen, optionally additional an adjuvant.

In certain embodiments, this disclosure relates to conjugates comprising a GM-CSF and IL-4 conjugate fused to a glycolipid (GPI)-anchoring sequence connected by a linker, e.g., polypeptide. In certain embodiments, the disclosure relates to isolated nucleic acids encoding these polypeptide conjugates, vectors comprising nucleic acid encoding the fusion proteins, and protein expression systems comprising these vectors, e.g., recombinant infectious viral particles and host cells comprising such nucleic acids.

In some embodiments, the vaccine comprises, or is the antigenic component of, a live attenuated virus, killed virus, a virus-like particle, virosome, and the antigen is typically a viral protein or glycoprotein.

In certain embodiments, the disclosure relates to methods of treating or preventing a viral infection comprising administering an effective amount of a pharmaceutical composition comprising a chimeric virus-like particle comprising GM-CSF and IL-4 conjugate fused to a glycolipid (GPI)-anchoring sequence optionally in combination with a vaccine or antigen and optionally an adjuvant. In certain embodiments, the subject is at risk or, exhibiting symptoms of, or diagnosed with a viral infection, such as a chronic viral infection.

In certain embodiments, the disclosure relates to methods of treating or preventing a viral infection comprising administering an effective amount of a vaccine comprising a chimeric virus- homologous like particle comprising GM-CSF and IL-4 conjugate fused to a glycolipid (GPI)-anchoring sequence wherein the subject is diagnosed with influenza A virus including subtype H1N1, influenza B virus, influenza C virus, rotavirus A, rotavirus B, rotavirus C, rotavirus D, rotavirus E, SARS coronavirus, human adenovirus types (HAdV-1 to 55), human papillomavirus (HPV) Types 16, 18, 31, 33, 35, 39, 45, 51, 52, 56, 58, and 59, parvovirus B19, molluscum contagiosum virus, JC virus (JCV), BK virus, Merkel cell polyomavirus, coxsackie A virus, norovirus, Rubella virus, lymphocytic choriomeningitis virus (LCMV), yellow fever virus, measles virus, mumps virus, respiratory syncytial virus, rinderpest virus, California encephalitis virus, hantavirus, rabies virus, ebola virus, marburg virus, herpes simplex virus-1 (HSV-1), herpes simplex virus-2 (HSV-2), varicella zoster virus (VZV), Epstein-Barr virus (EBV), cytomegalovirus (CMV), herpes lymphotropic virus, roseolovirus, or Kaposi's sarcoma-associated herpesvirus, hepatitis A, hepatitis B, hepatitis C, hepatitis D, hepatitis E, or human immunodeficiency virus (HIV).

In certain embodiments, the disclosure relates to administering a chimeric virus-like particle comprising GM-CSF and IL-4 conjugate fused to a glycolipid (GPI)-anchoring sequence in combination with an antiviral agent such as abacavir, acyclovir, acyclovir, adefovir, amantadine, amprenavir, ampligen, arbidol, atazanavir, atripla, boceprevir, cidofovir, combivir,darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type II, interferon type I, lamivudine, lopinavir, loviride, maraviroc, moroxydine, methisazone, nelfinavir, nevirapine, nexavir, oseltamivir, peginterferon alfa-2a, penciclovir, peramivir, pleconaril, podophyllotoxin, raltegravir, ribavirin, rimantadine, ritonavir, pyramidine, saquinavir, stavudine, tenofovir, tenofovir disoproxil, tipranavir, trifluridine, trizivir, tromantadine, truvada, valaciclovir, valganciclovir, vicriviroc, vidarabine, viramidine zalcitabine, zanamivir, and/or zidovudine.

In certain embodiments, the disclosure relates to gene therapies comprising administering vectors comprising nucleic acid encoding conjugates disclosed herein to a subject in need thereof. In certain embodiments, the nucleic acids are isolated and/or purified from their natural state or translated to a non-naturally occurring form such as cDNA.

In certain embodiments, it is contemplated that chimeric virus-like particles disclosed herein may contain other surface polypeptides, antigens and co-stimulatory molecules such as B7-1, B7-2, ICAM-1, and/or IL-2. It is contemplated that these particles may be used in all the applications that chimeric virus-like particles disclosed herein are mentioned.

Within certain embodiments, GM-CSF and IL-4 conjugates fused to a glycolipid (GPI)-anchoring sequence may be further conjugated to an adjuvant, cytokine, co-stimulatory molecule, antigen, protein, or glycoprotein. In certain embodiments, the antigen is a viral protein.

In certain embodiments, the viral protein or antigen is selected from an influenza virus hemagglutinin and neuraminidase; cytomegalovirus glycoprotein gB, p28, p38, p50, p52, p65, and p150; Borrelia p41; HIV nef, integrase, gag, protease, tat, env, p31, p17, p24, p31, p55, p66, gp32, gp36, gp39, gp41, gp120, and gp160; SIV p55; HBV core, surface antigen, and australian antigen; HCV core nucleocapsid, NS3, NS4, and NS5; Dengue env and NS1; EBV early antigen, p18, p23, gp125, nuclear antigen (EBNA)-1, EBNA-2, EBNA-3A, EBNA-3B, EBNA-3C, EBNA-leader protein (EBNA-LP), latent membrane proteins (LMP)-1, LMP-2A and LMP-2B; and herpes simplex virus gD and gG or fragments or mutated forms thereof.

In certain embodiments, the adjuvant or cytokine is selected from IL-2, IL-12, IL-15, IL-7, IL-18, IL-21, IL-27, IL-31, IFN-alpha, flagellin, unmethylated, CpG oligonucleotide, lipopolysaccharides, lipid A, and heat stable antigen (HSA).

In certain embodiments, the disclosure contemplates administration of pharmaceutical products comprising chimeric virus-like particles disclosed herein by intranasal (IN), intravenous (IV), subcutaneous (SC), or intraperitoneal (IP) administration.

GPI anchor were fused at the 5'- and 3'-ends of GIFT4 encoding DNA, respectively, to form the full-length gene.

Figure 1A:
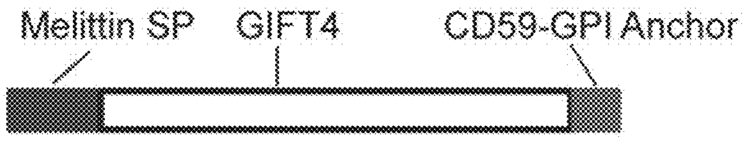
FIG. 1A illustrates the GPI-GIFT4 encoding gene. Coding sequences for the melittin signal peptide and murine CD59-
Figure 1B:
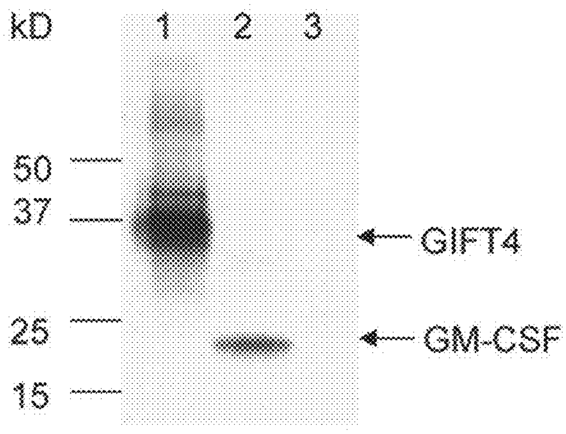

FIG. 1B shows data on the GPI-GIFT4 cellular expression. Western blots were developed with anti-GM-CSF antibody. Lane 1, whole cell lysate of GPI-GIFT4-expressing rBV infected insect cell sample; Lane 2, purified GM-CSF protein; Lane 3, whole cell lysate of HIV Env-expressing rBV infected cells as a control.

Figure 2:
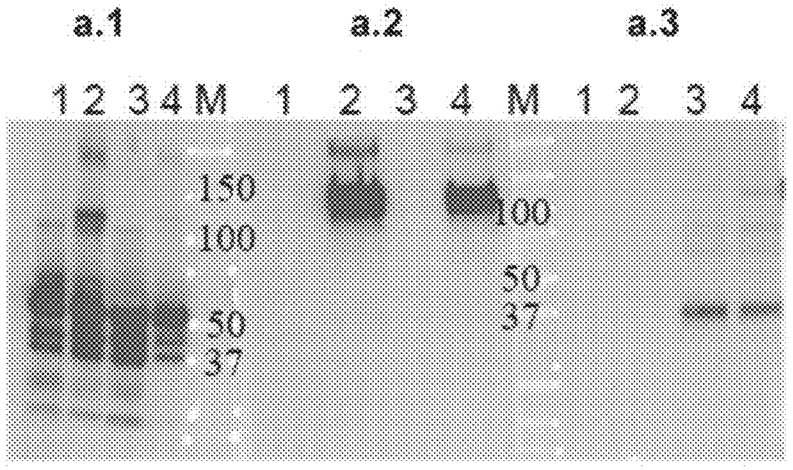

FIG. 2 shows western blotting analysis of the protein components of VLPs. VLP samples containing 1 μg of total protein were loaded for SDS-PAGE followed by western blotting. The Env incorporated into standard Env/Gag VLPs (sVLPs, lane 2) or cVLPs (lane 4) was observed to have a molecular mass of about 120 kDa. Protein bands were probed with: a.1, anti-HIV Gag antibody; a.2, anti-gp120 polyclonal antibodies; a.3, anti-GM-CSF antibody. Lane 1, Gag only VLPs; Lane 2, sVLPs; Lane 3, GIFT4/Gag VLPs; lane 4, cVLPs; M, Molecular weight (kDs).

Figure 3A:
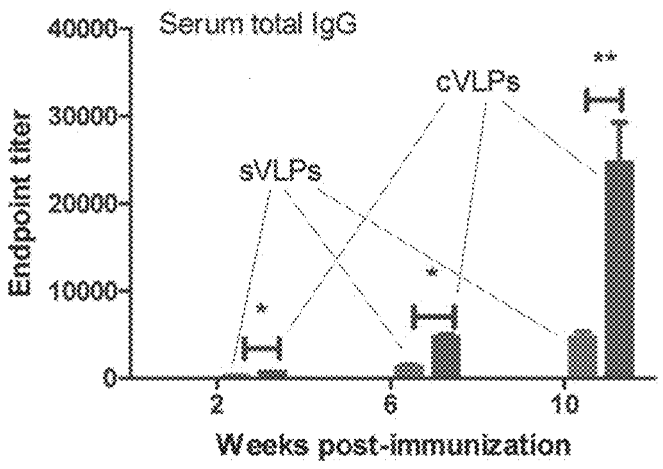

FIG. 3A shows data on serum endpoint titers. Guinea pigs were immunized with Gag only VLPs, GIFT4/Gag VLPs, sVLPs, or cVLPs (Left to Right) in the one i.m. priming-two i.n. boosting route at weeks 0, 4, 8, respectively, and immune sere were collected 2 weeks after each immunization at weeks 2, 6, 10, respectively.

Figure 3B:
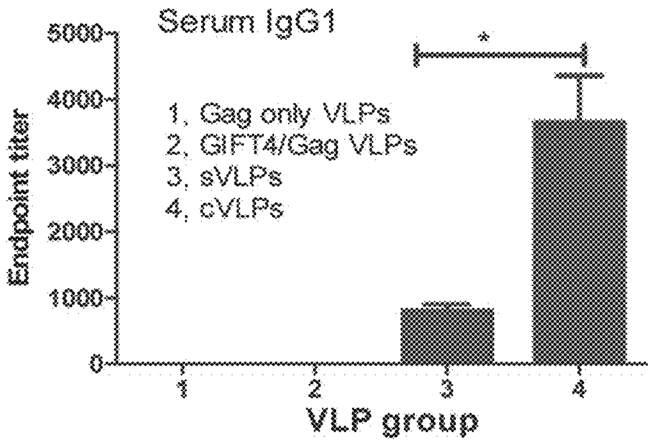

FIG. 3B shows data for IgG1 titers of immune sera from the bleed (week 10).

Figure 3C:
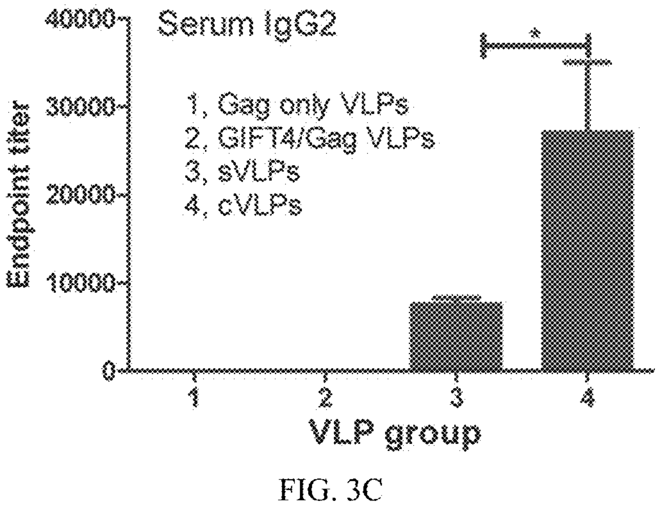

FIG. 3C shows data for IgG2 endpoint titers of immune sera from the bleed (week 10) as in FIG. 3A.

Figure 4A:
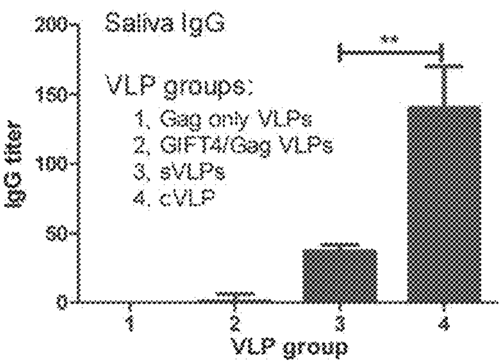

FIG. 4A shows data on mucosal antibody endpoint titers (saliva IgG). Mucosal samples were collected at week 12, 4 weeks after the last boosting immunization. Env-specific IgG and IgA endpoint titers were detected by ELISA as described in Materials and Methods.

Figure 4B:
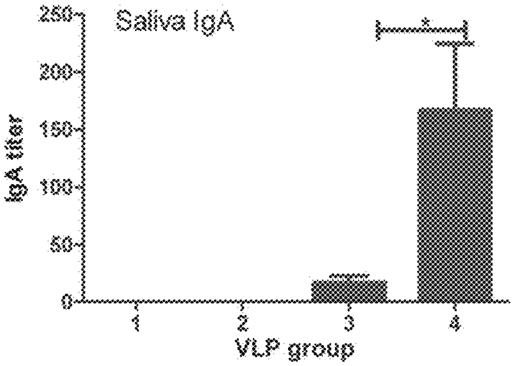

FIG. 4B shows data for saliva IgA as in FIG. 4A.

Figure 4C:
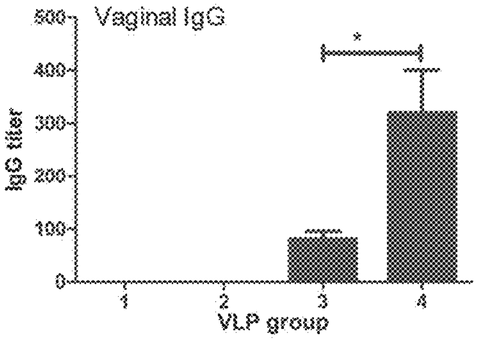

FIG. 4C shows data for vaginal IgG as in FIG. 4A.

Figure 4D:
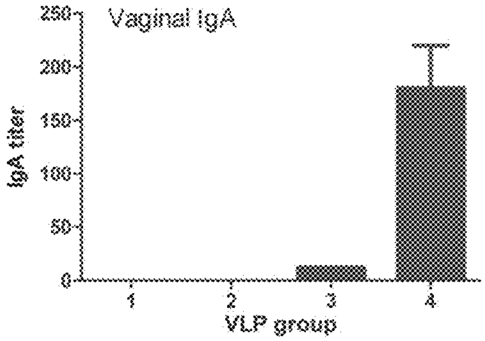

FIG. 4D shows data for vaginal IgA as in FIG. 4A.

Figure 5A:
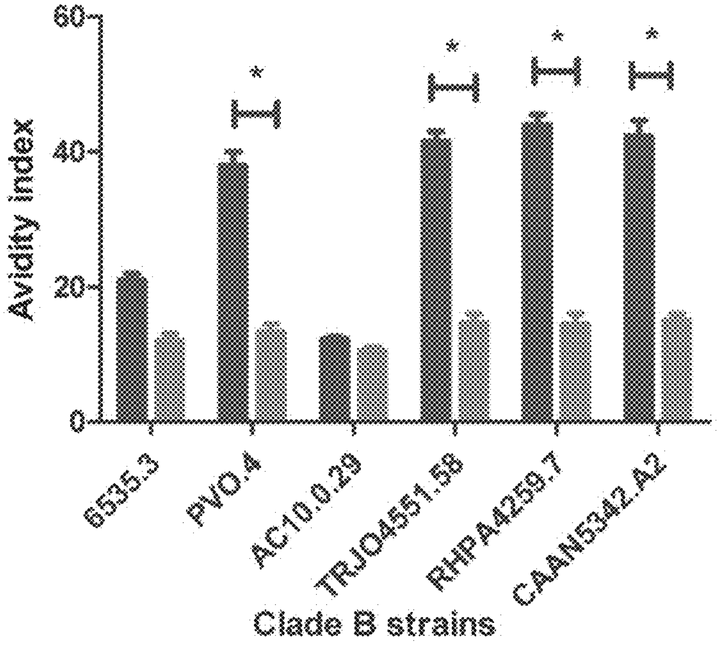

FIG. 5A shows avidity indexes of immune serum IgG to clade B pseudoviruses Avidity assays were conducted with immune sera of bleed 3 (at week 10) from sVLP (Right) and cVLPs (Left)-immunized guinea pigs.

Figure 5B:
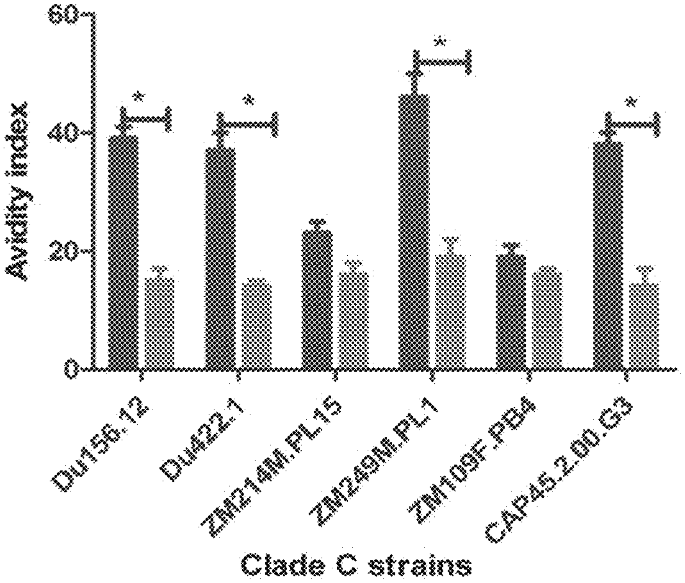

FIG. 5B shows avidity indexes of immune serum IgG to clade C pseudoviruses as in FIG. 5A.

Figure 6A:
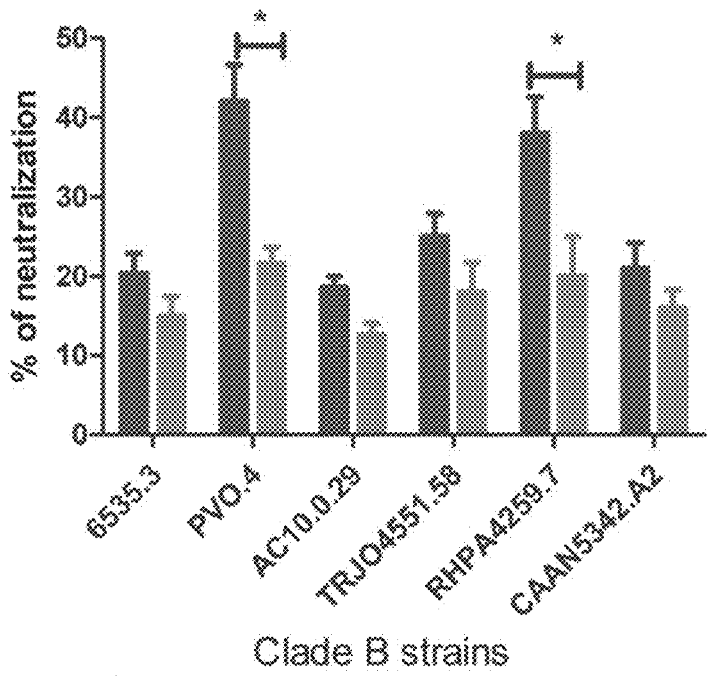

FIG. 6A shows data on neutralizing activity against clade B pseudoviruses. Immune sera of the bleed 3 from sVLPs (Right) and cVLPs (Left)-immunized animals were tested for neutralizing activity. The final dilution factor of immune sera was 40-fold.

Figure 6B:
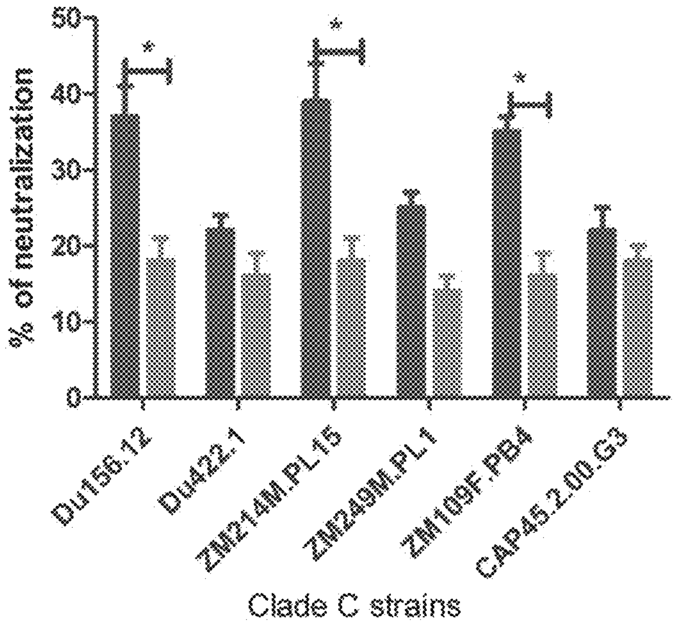

FIG. 6B shows data on neutralization against clade C pseudoviruses as in FIG. 6A.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

As used herein, the term "conjugate" refers to molecular entities joined by covalent bonds or other arrangement that provides substantially irreversible binding under physiological conditions. For example, two proteins, isolated and/or purified polypeptide sequence, may be conjugated together by a linker polymer, e.g., amino acid, polypeptide sequence, ethylene glycol polymer. Two proteins may be conjugated together by linking one protein to a ligand and linking the second protein to a receptor, e.g., streptavidin and biotin or an antibody and an epitope.

As used herein, the term "combination with" when used to describe administration with an additional treatment means that the agent may be administered prior to, together with, or after the additional treatment, or a combination thereof.

As used herein, "subject" refers to any animal, typically a human patient, livestock, or domestic pet.

As used herein, the terms "prevent" and "preventing" include the prevention of the recurrence, spread or onset. It is not intended that the present disclosure be limited to complete prevention. In some embodiments, the onset is delayed, or the severity is reduced.

As used herein, the terms "treat" and "treating" are not limited to the case where the subject (e.g. patient) is cured and the disease is eradicated. Rather, embodiments of the present disclosure also contemplate treatment that merely reduces symptoms, and/or delays disease progression.

As used herein, "amino acid sequence" refers to an amino acid sequence of a protein molecule. An "amino acid sequence" can be deduced from the nucleic acid sequence encoding the protein. However, terms such as "polypeptide" or "protein" are not meant to limit the amino acid sequence to the deduced amino acid sequence, but include non-naturally occurring amino acids, post-translational modifications of the deduced amino acid sequences, such as amino acid deletions, additions, and modifications such as glycosylation and addition of lipid moieties.

The term "a nucleic acid sequence encoding" a specified polypeptide refers to a nucleic acid sequence comprising the coding region of a gene or in other words the nucleic acid sequence which encodes a gene product. The coding region may be present in a cDNA, genomic DNA or RNA form. When present in a DNA form, the oligonucleotide, polynucleotide, or nucleic acid may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present disclosure may contain endogenous enhancers/promoters, splice junctions, intervening sequences, polyadenylation signals, etc. or a combination of both endogenous and exogenous control elements.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

A "virus-like particle" refers to a particle comprising virion proteins but is substantially free of viral genetic material, e.g., viral RNA. Virus-like particles may contain viral proteins from different viruses. See e.g., Guo et al., Enhancement of mucosal immune responses by chimeric influenza HA/SHIV virus-like particles, Virology, 2003, 313(2):502-13. Virus-like particles may contain lipid membranes and may be constructed to express a variety of antigens on their particle surface ether by expression in viral vectors use to create the particles or by mixing the virus-like particle with an antigen or other polypeptide conjugated to a glycosylphosphatidyl-inositol anchor. See e.g. Skountzou et al., J. Virol., 2007, 81(3):1083-94; Derdak et al., PNAS, 2006, 103(35) 13144-13149; Poloso et al., Molecular Immunol, 2001, 38:803-816.

Incorporation of a GPI-Anchored Engineered Cytokine as a Molecular Adjuvant Enhances the Immunogenicity of HIV VLPs Wang et al. report incorporation of chimeric human immunodeficiency virus envelope glycoproteins into virus-like particles. J Virol, 2007, 81, 10869-10878. A fusokine (fusion protein from two cytokines) from GM-CSF and IL4 (GIFT4) leads to B-cell effector function manifest by an altered pro-immune cytokine secretory profile and a B-cell mitogenic response. See Deng, et al. Cancer Res, 74, 4133-4144 (2014). A membrane-bound form of GIFT4 was generated by fusing the CD59 glycolipid (glycosylphosphatidyl-inositol, GPI) signal sequence to the GIFT4 C-terminal sequence in frame, and incorporated the membrane-anchored GIFT4 into Env-enriched VLPs. These chimeric VLPs (cVLPs) harboring both a high density of Env and membrane-anchored GIFT4 elicited highly augmented Env-specific antibody responses with improved quality, as reflected by enhanced avidity and neutralization activity.

A goal of developing vaccines against HIV is to elicit immune responses at the level of the mucosal surface to block transmission, as well as in systemic compartments to clear disseminated viruses. Vaccines administered by systemic routes generally fail to stimulate strong mucosal immune responses. Chimeric VLPs were developed with efficient co-incorporation of HIV Env together with a fusokine, GIFT4, as a co-stimulatory factor, into the same particles. The resulting cVLPs were evaluated for their capacity to elicit enhanced antibody responses in systemic compartments as well as mucosal surfaces. This disclosure integrates several approaches to enhance HIV immune responses. These include: 1) enhanced incorporation of Env into VLPs to increase the density of immunogens; 2) construction and co-incorporation of a membrane-bound form of GIFT4 into cVLPs to further improve immunogenicity by stimulating B lymphocyte proliferation and activation; 3) employment of a systemic prime/mucosal boost route to induced systemic as well as mucosal immune responses.

Vaccines are typically administered by intramuscular injection, and induce systemic immune responses. However, mucosal immunity is rarely induced by systemic immunization. Since mucosal transmission is the predominant pathway for HIV infection and accounts for as high as 80% of AIDS incidence globally, immunity functioning at the mucosal portals of entry is important for preventing primary HIV-1 infection. Because of the relatively low efficiency of HIV infection at mucosal surfaces, even a modest enhancement of antibody-mediated protective mucosal immune responses could have a significant effect on reducing disease incidence. Thus an effective HIV vaccine may need to induce both mucosal immunity to reduce the frequency of initial infection and possibly block the escape of virus from the genital and intestinal mucosa into systemic lymphoid organs, and systemic immunity, such as broadly neutralizing antibody responses, to clear any disseminated virus.

An intramuscular prime-intranasal boost immunization route was employed to induced enhance immunity both at systemic compartments and mucosal surfaces. Germinal centers containing B, T, plasma, and professional antigen presenting cells (APCs) are present in the nasal cavity. Lymphoid tissues strategically positioned at the site of entry of the respiratory and the digestive tracts are important in antigen uptake. By two i.n. boosts with the constructed cVLPs, highly elevated mucosal HIV Env-specific IgG and IgA levels were induced compared to sVLPs administered by the same route. The antibodies secreted into the lumen provide an immunological barrier to limit the penetration of antigens into mucous membranes and are associated with protection from HIV-1 infection. Although mucosal IgA and IgG responses were observed in animals immunized with cVLPs, serum IgA was not induced.

In a recent analysis of immune correlates in the RV144 trial, serum IgA levels were found to be inversely correlated to HIV protection. See Haynes et al. Immune-correlates analysis of an HIV-1 vaccine efficacy trial. NEJM, 2012, 366, 1275-1286. Low serum IgA levels in immune sera may therefore be an advantageous consequence of GIFT4-containing VLP-induced immunity.

A desirable antibody response should include high titers of antibodies with high antibody avidity and neutralizing activity. Enhanced antibody avidity and neutralizing breadth and potency in the cVLP-immunized group was observed, supporting the conclusion that the adjuvant effect of GPI-GIFT4 enables the immune system to more effectively process or present B cell epitopes residing in Env. The enhanced avidity observed may be contributed by non-neutralizing antibodies.

GM-CSF and IL-4 Conjugate (GIFT4) Fused to a Glycolipid (GPI)-Anchoring Sequence (GPI-GIFT4) that is Incorporated into Chimeric Virus-Like Particles (cVLPs) Enriched with a Viral Antigen Some exemplary methods of making GM-CSF and IL-4 conjugate fused to a glycolipid (GPI)-anchoring sequence that is incorporated into chimeric virus-like particles (cVLPs) are described below. Methods useful for the making VLPs of the present disclosure for administration with vaccines, viral proteins, antigens and adjuvant molecules of the present disclosure, or which incorporate viral proteins, antigen, or adjuvant molecules into the VLP, may be found in U.S. Pat. Nos. 8,795,682; 6,077,662; WO 2004/042001, which are herein incorporated by reference in their entireties, and which are also described below.

VLPs for use in the immunogenic compositions of the present disclosure can be produced by in vitro cell culture expression systems such as, but not limited to, recombinant baculovirus expression system (BEVS) (see, for example, Yamshchikov et al., (1995) Virology: 214, 50-58). Assembly of HIV or SIV virus-like particles containing envelope proteins may be performed using expression systems, such as, but not limited to, a baculovirus expression system (Yamshchikov et al., (1995) Virology: 214, 50-58), recombinant poxvirus expression system (MVA) (Wyatt et al., (1996), Vaccine: 15, 1451-1458), recombinant VSV, recombinant adenovirus, and recombinant DNA expression vectors. Preferably, the VLPs are produced using recombinant BEVS and recombinant poxvirus expression systems.

In general, VLPs can be produced by simultaneously introducing into a cell a viral core protein expression vector, a viral surface envelope glycoprotein expression vector, and/or an expression vector encoding GPI-GIFT4. The expressed viral core protein self-assembles into a VLP that incorporates the viral surface envelope glycoprotein and/or the GPI-GIFT4. The viral surface envelope glycoprotein and/or the adjuvant molecule are expressed and disposed on the VLP surface. Thereafter, the cell produces the VLP (for example, Vero cells, chimeric and/or phenotypically mixed VLPs). The cells may be selected from, but are not limited to, insect cells (e.g., Spodopera frugiperda Sf9 and Sf21 cells), and mammalian cells such as, but not limited to, EL4 cells and HeLa cells. The expression elements for expressing the viral core protein, viral surface envelope glycoprotein, and GPI-GIFT4 can also be included together in a single expression vector, or can be included in two or more expression vectors.

In general, the viral protein expression vector can be produced by operably linking a coding sequence for a viral protein of a virus to an appropriate promoter (e.g., an early promoter, late promoter, or hybrid late/very late promoter). The viral protein expression vector can also be modified to form a viral protein expression construct. In addition, the viral surface envelope glycoprotein expression vector can be produced by operably linking a coding sequence for a viral surface envelope glycoprotein of a virus to an appropriate promoter (e.g., early promoter, late promoter, or hybrid late/very late promoter). The viral surface envelope glycoprotein expression vector can be modified to form a viral surface envelope glycoprotein expression construct. Similarly, the GPI-GIFT4 expression vector can be produced by operably linking a coding sequence for GPI-GIFT4 to an appropriate promoter (e.g., early promoter, late promoter, or hybrid late/very late promoter). The GPI-GIFT4 expression vector can be modified to form an GPI-GIFT4 expression construct.

In other embodiments of the disclosure, nucleic acid sequences encoding for a viral core protein, at least one viral surface envelope protein, and GPI-GIFT4 can be included in a single expression vector, or in two or more expression vectors. The one or more expression vectors can be introduced into a host cell, the proteins can be expressed in the cell, whereby the cell forms the VLP. In embodiments, each of the nucleic acid sequences encoding for the viral core protein, the viral surface envelope glycoprotein, and the GPI-GIFT4 is operably linked to an appropriate promoter (e.g., a baculovirus promoter, a recombinant Modified Vaccinia Ankara (MVA) promoter, a CMV promoter, an EF promoter, an adenovirus promoter, a recombinant VSV promoter, a recombinant adenovirus promoter, a recombinant alphavirus promoter, and a recombinant DNA expression vector). Appropriate promoters include, but are not limited to, a constitutive or inducible promoter; an early, late, or hybrid late/very late promoter.

An embodiment of this disclosure, GPI-GIFT4 comprises a human GM-CSF, MWLQSLLLLGTV ACSISAPARS PSPSTQPWEHVNAI QEARRLLN LSRDTAAEMN ETVEVISE MFDLQEPTC LQTRLELYKQGL RGSLT-KLKGPLTMMASH YKQHCPPETSCATQ TITFESF KENLKDFLLVIPFDCWEPVQE (SEQ ID NO: 1) sequence and a human IL-4. In certain embodiments, the disclosure contemplates a fusokine with a recombinant human form such as isoform 1 which is amino acids sequence MGLTSQLLPP LFFLLACAGN FVHGHKCDIT LQEIIKTLNS LTEQKTLCTE LTVTDIFAAS KNT-TEKETFC RAATVLRQFY SHHEKDTRCL GATAQQF-HRH KQLIRFLKRL DRNLWGLAGL NSCPVKEANQ STLENFLERL KTIMREKYSK CSS (SEQ ID NO: 2) or isoform 2 which is amino acid sequence MGLTSQLLPP LFFLLACAGN FVHGHKCDIT LQEIIKTLNS LTE-QKNTTEK ETFCRAATVL RQFYSHHEKD TRCLGA-TAQQ FHRHKQLIRF LKRLDRNLWG LAGLNSCPVK EANQSTLENFLERLKTIMRE KYSKCSS (SEQ ID NO: 3). Isoform 2 lacks an in-frame exon in the 5' region, compared to variant 1, resulting an isoform (2) that lacks an internal region, as compared to isoform 1.

The present disclosure encompasses fusion proteins involving full-length pre-processed forms, as well as mature processed forms, fragments thereof and variants of each or both of the GM-C SF and IL-4 entities with linker amino acids, including allelic as well as non-naturally occurring variants. In addition to naturally-occurring allelic variants of the GM-CSF and IL-4 entities that may exist in the population, the skilled artisan will further appreciate that changes (i.e. one or more deletions, additions and/or substitutions of one or more amino acid) can be introduced by mutation using classic or recombinant techniques to effect random or targeted mutagenesis. A suitable variant in use in the present disclosure typically has an amino acid sequence having a high degree of homology with the amino acid sequence of the corresponding native cytokine. In one embodiment, the amino acid sequence of the variant cytokine in use in the fusion protein of the disclosure is at least 70%, at least about 75%, at least about 80%, at least about 90%, typically at least about 95%, more typically at least about 97% and even more typically at least about 99% identical to the corresponding native sequence, e.g., SEQ ID NO: 7. In certain embodiments, such native sequence is of human GM-CSF and/or human IL-4.

Percent identities between amino acid or nucleic acid sequences can be determined using standard methods known to those of skill in the art. For instance for determining the percentage of homology between two amino acid sequences, the sequences are aligned for optimal comparison purposes. The amino acid residues at corresponding amino acid positions are then compared. Gaps can be introduced in one or both amino acid sequence(s) for optimal alignment and non-homologous sequences can be disregarded for comparison purposes. When a position in the first sequence is occupied by the same amino acid residue as the corresponding position in the second sequence, then the sequences are identical at that position. The percent identity between the two sequences is a function of the number of identical positions shared by the sequences, taking into account the number of gaps which need to be introduced for optimal alignment and the length of each gap. The comparison of sequences and determination of percent identity and similarity between two sequences can be accomplished using a mathematical algorithm (e.g. Computational Molecular Biology, 1988, Ed Lesk A M, Oxford University Press, New York; Biocomputing: Informatics and Genome Projects, 1993, Ed Smith D. W., Academic Press, New York; Computer Analysis of Sequence Data, 1994, Eds Griffin A. M. and Griffin H. G., Human Press, New Jersey; Sequence Analysis Primer, 1991, Eds Griskov M. and Devereux J., Stockton Press, New York). Moreover, various computer programs are available to determine percentage identities between amino acid sequences and between nucleic acid sequences, such as GCG™ program (available from Genetics Computer Group, Madison, Wis.), DNAsis™ program (available from Hitachi Software, San Bruno, Calif.) or the MacVector™ program (available from the Eastman Kodak Company, New Haven, Conn.).

Suitable variants of GM-CSF and IL-4 entities for use in the present disclosure are biologically active and retain at least one of the activities described herein in connection with the corresponding polypeptide. Typically, the therapeutic effect is preserved, although a given function of the polypeptide(s) may be positively or negatively affected to some degree, e.g. with variants exhibiting reduced cytotoxicity or enhanced biological activity. Amino acids that are essential for a given function can be identified by methods known in the art, such as by site-directed mutagenesis. Amino acids that are critical for binding a partner/substrate (e.g. a receptor) can also be determined by structural analysis such as crystallization, nuclear magnetic resonance and/or photoaffinity labeling. The resulting variant can be tested for biological activity in assays such as those described above.

For example, in one class of functional variants, one or more amino acid residues are conservatively substituted. A "conservative amino acid substitution" is one in which the amino acid residue in the native polypeptide is replaced with an amino acid residue having a similar side chain. Families of amino acid residues having similar side chains have been defined in the art. Typically, substitutions are regarded as conservative when the replacement, one for another, is among the aliphatic amino acids Ala, Val, Leu, and Ile; the hydroxyl residues Ser and Thr; the acidic residues Asp and Glu; the amide residues Asn and Gln; the basic residues Lys and Arg; or the aromatic residues Phe and Tyr. Alternatively, in another embodiment, mutations can be introduced randomly along all or part of a cytokine coding sequence, such as by saturation mutagenesis, and the resultant mutant can be screened for its biological activity as described herein to identify mutants that retain at least therapeutic activity.

Although the GM-C SF and IL-4 entities can be directly fused in the fusion protein of the disclosure, it is however typical to use a linker for joining GM-CSF and IL-4. The purpose of the linker is to allow the correct formation, folding and/or functioning of each of the GM-CSF and IL-4 entities. It should be sufficiently flexible and sufficiently long to achieve that purpose. Typically, the coding sequence of the linker may be chosen such that it encourages translational pausing and therefore independent folding of the GM-CSF and IL-4 entities. A person skilled in the art will be able to design suitable linkers in accordance with the disclosure. Certain embodiments of the disclosure are not limited by the form, size or number of linker sequences employed. Multiple copies of the linker sequence of choice may be inserted between GM-CSF and IL-4. The only requirement for the linker sequence is that it functionally does not adversely interfere with the folding and/or functioning of the individual entities of the fusion protein. For example, a suitable linker is 1 to 5 or 5 to 50 amino acid long and may comprise amino acids such as glycine, serine, threonine, asparagine, alanine and proline (see for example Wiederrecht et al., 1988, Cell 54, 841; Dekker et al., 1993, Nature 362, 852; Sturm et al., 1988, Genes and Dev. 2, 1582; Aumailly et al., 1990 FEBS Lett. 262, 82). Repeats comprising serine and glycine residues are typical in the context of the disclosure. Specific examples of suitable linkers consists of two or three or more (e.g. up to eight or more) copies of the sequence Gly-Gly-Gly-Gly-Ser (GGGGS) (SEQ ID NO: 4). It will be evident that the disclosure is not limited to the use of these particular linkers.

The disclosure further includes fusion proteins which comprise, or alternatively consist essentially of, or alternatively consist of an amino acid sequence which is at least 70%, 75%, 80%, 90%, 95%, 97%, 99% homologous or even better 100% homologous (identical) to all or part of any of the amino acid sequences recited in SEQ ID NO: 1-7.

In the context of the present disclosure, a protein "consists of" an amino acid sequence when the protein does not contain any amino acids but the recited amino acid sequence. A protein "consists essentially of" an amino acid sequence when such an amino acid sequence is present together with only a few additional amino acid residues, typically from about 1 to about 50 or so additional residues. A protein "comprises" an amino acid sequence when the amino acid sequence is at least part of the final (i.e. mature) amino acid sequence of the protein. Such a protein can have a few up to several hundred additional amino acids residues. Such additional amino acid residues can be naturally associated with each or both entities contained in the fusion or heterologous amino acid/peptide sequences (heterologous with respect to the respective entities). Such additional amino acid residues may play a role in processing of the fusion protein from a precursor to a mature form, may facilitate protein trafficking, prolong or shorten protein half-life or facilitate manipulation of the fusion protein for assay or production, among other things. Typically, the fusion proteins of the disclosure comprise a signal peptide at the $NH_2$-terminus in order to promote secretion in the host cell or organism. For example, the endogenous signal peptide (i.e. naturally present in the cytokine present at the $NH_2$ terminus of said fusion) can be used or alternatively a suitable heterologous (with respect to the cytokine in question) signal peptide sequence can be added to the cytokine entity present at the $NH_2$ terminus of the fusion or inserted in replacement of the endogenous one.

In the context of the disclosure, the fusion proteins of the disclosure can comprise cytokine entities of any origin, i.e. any human or animal source (including canine, avian, bovine, murine, ovine, feline, porcine, etc). Although "chimeric" fusion proteins are also encompassed by the disclosure (e.g. one cytokine entity of human origin and the other of an animal source), it is typical that each entity be of the same origin (e.g. both from humans).

The fusion proteins of the present disclosure can be produced by standard techniques. Polypeptide and DNA sequences for each of the cytokines involved in the fusion protein of the present disclosure are published in the art, as are methods for obtaining expression thereof through recombinant or chemical synthetic techniques. In another embodiment, a fusion-encoding DNA sequence can be synthesized by conventional techniques including automated DNA synthesizers. Then, the DNA sequence encoding the fusion protein may be constructed in a vector and operably linked to a regulatory region capable of controlling expression of the fusion protein in a host cell or organism. Techniques for cloning DNA sequences for instance in viral vectors or plasmids are known to those of skill in the art (Sambrook et al, 2001, "Molecular Cloning. A Laboratory Manual", Laboratory Press, Cold Spring Harbor N.Y.). The fusion protein of the disclosure can be purified from cells that have been transformed to express it.

The present disclosure also provides a nucleic acid molecule encoding the fusion protein of the disclosure. Within the context of the present disclosure, the term "nucleic acid" and "polynucleotide" are used interchangeably and define a polymer of nucleotides of any length, either deoxyribonucleotide (DNA) molecules (e.g., cDNA or genomic DNA) and ribonucleotide (RNA) molecules (e.g., mRNA) and analogs of the DNA or RNA generated using nucleotide analogs (see U.S. Pat. Nos. 5,525,711 and 4,711,955 as examples of nucleotide analogs). If present, modifications to the nucleotide structure may be imparted before or after assembly of the polymer. The sequence of nucleotides may also be interrupted by non-nucleotide elements. The nucleic acid molecule may be further modified after polymerization, such as by conjugation with a labeling component. The nucleic acid, especially DNA, can be double-stranded or single-stranded, but typically is double-stranded DNA. Single-stranded nucleic acids can be the coding strand (sense strand) or the non-coding strand (anti-sense strand).

The nucleic acid molecules of the disclosure include, but are not limited to, the sequence encoding the fusion protein alone, but may comprise additional non-coding sequences, for example introns and non-coding 5' and 3' sequences that play a role in transcription, mRNA processing (including splicing and polyadenylation signals), ribosome binding and mRNA stability. For example, the nucleic acid molecule of the disclosure can contain less than about 5 kb, 4 kb, 3 kb, 2 kb, 1 kb, 0.5 kb or 0.1 kb of nucleotide sequences which naturally flank (i.e. sequences located at the 5' and 3' ends) or are present within the genomic DNA encoding GM-CSF and IL-4 entities.

According to a typical embodiment, the present disclosure provides nucleic acid molecules which comprise, or alternatively consist essentially of, or alternatively consist of a nucleotide sequence encoding all or part of an amino acid sequence encoding a fusion protein which is at least about 70%, at least about 75%, at least about 80%, at least about 90%, at least about 95%, typically at least about 97%, more typically at least about 99% homologous or even more typically 100% homologous to any of the amino acid sequences shown in SEQ ID NO: 1-7.

In another embodiment, a nucleic acid molecule of the disclosure comprises a nucleic acid molecule which is a complement of all or part of a nucleotide sequence encoding the fusion protein shown in any of SEQ ID NO: 1-7. A nucleic acid molecule which is complementary to the nucleotide sequence of the present disclosure is one which is sufficiently complementary such that it can hybridize to the fusion-encoding nucleotide sequence under stringent conditions, thereby forming a stable duplex. Such stringent conditions are known to those skilled in the art. A typical, non-limiting example of stringent hybridization conditions are hybridization in 6 times sodium chloride/sodium citrate (SSC) at about 45 C, followed by one or more washes in 0.2 times SSC, 0.1% SDS at 50-65 C. In one embodiment, the disclosure pertains to antisense nucleic acid to the nucleic acid molecules of the disclosure. The antisense nucleic acid can be complementary to an entire coding strand, or to only a portion thereof.

In still another embodiment, the disclosure encompasses variants of the above-described nucleic acid molecules of the disclosure e.g., that encode variants of the fusion proteins that are described above. The variation(s) encompassed by the present disclosure can be created by introducing one or more nucleotide substitutions, additions and/or deletions into the nucleotide sequence by standard techniques, such as site-directed mutagenesis and PCR-mediated mutagenesis. Following mutagenesis, the variant nucleic acid molecule can be expressed recombinantly as described herein and the activity of the resulting protein can be determined using, for example, assays described herein. Alternatively, the nucleic acid molecule of the disclosure can be altered to provide preferential codon usage for a specific host cell (for example *E. coli*; Wada et al., 1992, Nucleic Acids Res. 20, 2111-2118). The disclosure further encompasses nucleic acid molecules that differ due to the degeneracy of the genetic code and thus encode for example the same fusion protein as any of those shown in SEQ ID NO: 1-7.

Another embodiment of the disclosure pertains to fragments of the nucleic acid molecule of the disclosure, e.g. restriction endonuclease and PCR-generated fragments. Such fragments can be used as probes, primers or fragments encoding an immunogenic portion of the fusion protein.

The nucleic acid molecules of the present disclosure can be generated using the sequence information provided herein. The nucleic acid encoding each of the GM-CSF and IL-4 entities can be cloned or amplified using cDNA or, alternatively, genomic DNA, as a template and appropriate probes or oligonucleotide primers according to standard molecular biology techniques (e.g., as described in Sambrook, et al. "Molecular Cloning: A Laboratory Manual", Cold Spring Harbor Laboratory Press, Cold Spring Harbor, N.Y., 2001) or standard PCR amplification techniques based on sequence data accessible in the art (such as those provided above in connection with the fusion proteins of the disclosure or those provided in the Examples part). Fusing of the GM-CSF sequence to the IL-4 sequence may be accomplished as described in the Experimental below or by conventional techniques. For example, the GM-CSF and IL-4 encoding sequences can be ligated together in-frame either directly or through a sequence encoding a peptide linker. The GM-CSF-encoding sequence can also be inserted directly into a vector which contains the IL-4-encoding sequence, or vice versa. Alternatively, PCR amplification of the GM-C SF and IL-4-encoding sequences can be carried out using primers which give rise to complementary overhangs which can subsequently be annealed and re-amplified to generate a fusion gene sequence.

Pharmaceutical Compositions

As used herein the language "pharmaceutically acceptable excipient" is intended to include any and all carriers, solvents, diluents, excipients, adjuvants, dispersion media, coatings, antibacterial and antifungal agents, and absorption delaying agents, and the like, compatible with pharmaceutical administration.

Suitably, the pharmaceutical composition of the disclosure comprises a carrier and/or diluent appropriate for its delivering by injection to a human or animal organism. Such carrier and/or diluent is non-toxic at the dosage and concentration employed. It is selected from those usually employed to formulate compositions for parental administration in either unit dosage or multi-dose form or for direct infusion by continuous or periodic infusion. It is typically isotonic, hypotonic or weakly hypertonic and has a relatively low ionic strength, such as provided by sugars, polyalcohols and isotonic saline solutions. Representative examples include sterile water, physiological saline (e.g. sodium chloride), bacteriostatic water, Ringer's solution, glucose or saccharose solutions, Hank's solution, and other aqueous physiologically balanced salt solutions (see for example the most current edition of Remington: The Science and Practice of Pharmacy, A. Gennaro, Lippincott, Williams & Wilkins). The pH of the composition of the disclosure is suitably adjusted and buffered in order to be appropriate for use in humans or animals, typically at a physiological or slightly basic pH (between about pH 8 to about pH 9, with a special preference for pH 8.5). Suitable buffers include phosphate buffer (e.g. PBS), bicarbonate buffer and/or Tris buffer. A typical composition is formulated in 1M saccharose, 150 mM NaCl, 1 mM MgCl2, 54 mg/l Tween 80, 10 mM Tris pH 8.5. Another typical composition is formulated in 10 mg/ml mannitol, 1 mg/ml HSA, 20 mM Tris, pH 7.2, and 150 mM NaCl.

The composition of the disclosure can be in various forms, e.g. in solid (e.g. powder, lyophilized form), or liquid (e.g. aqueous). In the case of solid compositions, the typical methods of preparation are vacuum drying and freeze-drying which yields a powder of the active agent plus any additional desired ingredient from a previously sterile-filtered solution thereof. Such solutions can, if desired, be stored in a sterile ampoule ready for reconstitution by the addition of sterile water for ready injection.

Nebulized or aerosolized formulations also form part of this disclosure. Methods of intranasal administration are well known in the art, including the administration of a droplet, spray, or dry powdered form of the composition into the nasopharynx of the individual to be treated from a pressured container or dispenser which contains a suitable propellant, e.g., a gas such as carbon dioxide, or a nebulizer (see for example WO 95/11664). Enteric formulations such as gastroresistant capsules and granules for oral administration, suppositories for rectal or vaginal administration also form part of this disclosure. For non-parental administration, the compositions can also include absorption enhancers which increase the pore size of the mucosal membrane. Such absorption enhancers include sodium deoxycholate, sodium glycocholate, dimethyl-beta-cyclodextrin, lauroyl-1-lysophosphatidylcholine and other substances having structural similarities to the phospholipid domains of the mucosal membrane.

The composition can also contain other pharmaceutically acceptable excipients for providing desirable pharmaceutical or pharmacodynamic properties, including for example modifying or maintaining the pH, osmolarity, viscosity, clarity, color, sterility, stability, rate of dissolution of the formulation, modifying or maintaining release or absorption into an the human or animal organism. For example, polymers such as polyethylene glycol may be used to obtain desirable properties of solubility, stability, half-life and other pharmaceutically advantageous properties (Davis et al., 1978, Enzyme Eng. 4, 169-173; Burnham et al., 1994, Am. J. Hosp. Pharm. 51, 210-218). Representative examples of stabilizing components include polysorbate 80, L-arginine, polyvinylpyrrolidone, trehalose, and combinations thereof. Other stabilizing components especially suitable in plasmid-based compositions include hyaluronidase (which is thought to destabilize the extra cellular matrix of the host cells as described in WO 98/53853), chloroquine, protic compounds such as propylene glycol, polyethylene glycol, glycerol, ethanol, 1-methyl L-2-pyrrolidone or derivatives thereof, aprotic compounds such as dimethylsulfoxide (DMSO), diethylsulfoxide, di-n-propylsulfoxide, dimethylsulfone, sulfolane, dimethyl-formamide, dimethylacetamide, tetramethylurea, acetonitrile (see EP 890 362), nuclease inhibitors such as actin G (WO 99/56784) and cationic salts such as magnesium ($Mg^{2+}$) (EP 998 945) and lithium ($Li^{+}$) (WO 01/47563) and any of their derivatives. The amount of cationic salt in the composition of the disclosure typically ranges from about 0.1 mM to about 100 mM, and still more typically from about 0.1 mM to about 10 mM. Viscosity enhancing agents include sodium carboxymethylcellulose, sorbitol, and dextran. The composition can also contain substances known in the art to promote penetration or transport across the blood barrier or membrane of a particular organ (e.g. antibody to transferrin receptor; Friden et al., 1993, Science 259, 373-377). A gel complex of poly-lysine and lactose (Midoux et al., 1993, Nucleic Acid Res. 21, 871-878) or poloxamer 407 (Pastore, 1994, Circulation 90, 1-517) can be used to facilitate administration in arterial cells.

The composition of the disclosure may also comprise one or more adjuvant(s) suitable for systemic or mucosal application in humans. Representative examples of useful adjuvants include without limitation alum, mineral oil emulsion such as Freunds complete and incomplete, lipopolysaccharide or a derivative thereof (Ribi et al., 1986, Immunology and Immunopharmacology of Bacterial Endotoxins, Plenum Publ. Corp., NY, p407-419), saponins such as QS21 (Sumino et al., 1998, J. Virol. 72, 4931-4939; WO 98/56415), Escin, Digitonin, Gypsophila or Chenopodium quinoa saponins and CpG oligodeoxynucleotides. Alternatively the composition of the disclosure may be formulated with conventional vaccine vehicles composed of chitosan or other polycationic polymers, polylactide and polylactide-co-glycolide particles, poly-N-acetyl glucosamine-based polymer matrix, particles composed of polysaccharides or chemically modified polysaccharides, and lipid-based particles, etc. The composition may also be formulated in the presence of cholesterol to form particulate structures such as liposomes.

The composition may be administered to patients in an amount effective, especially to enhance an immune response in an animal or human organism. As used herein, the term "effective amount" refers to an amount sufficient to realize a desired biological effect. For example, an effective amount for enhancing an immune response could be that amount necessary to cause activation of the immune system.

The appropriate dosage may vary depending upon known factors such as the pharmacodynamic characteristics of the particular active agent, age, health, and weight of the host organism; the condition(s) to be treated, nature and extent of symptoms, kind of concurrent treatment, frequency of treatment, the need for prevention or therapy and/or the effect desired. The dosage will also be calculated dependent upon the particular route of administration selected. Further refinement of the calculations necessary to determine the appropriate dosage for treatment is routinely made by a practitioner, in the light of the relevant circumstances. The titer may be determined by conventional techniques. A composition based on vector plasmids may be formulated in the form of doses of between 1 □g to 100 mg, advantageously between 10 □g and 10 mg and typically between 100 □g and 1 mg. A composition based on proteins may be formulated in the form of doses of between 10 ng to 100 mg. A typical dose is from about 1 □g to about 10 mg of the therapeutic protein per kg body weight. The administration may take place in a single dose or a dose repeated one or several times after a certain time interval. In one typical embodiment, the composition of the present disclosure is administered by injection using conventional syringes and needles, or devices designed for ballistic delivery of solid compositions (WO 99/27961), or needleless pressure liquid jet device (U.S. Pat. Nos. 4,596,556; 5,993,412).

The composition of the disclosure can be enclosed in ampoules, disposable syringes or multiple dose vials made of glass or plastic. In all cases, the composition must be sterile and should be fluid to the extent that easy syringability exists. It must be stable under the conditions of manufacture and storage and must be preserved against the contaminating action of microorganisms such as bacteria and fungi. Sterile injectable solutions can be prepared by incorporating the active agent (e.g., a fusion protein or infectious particles) in the required amount with one or a combination of ingredients enumerated above, followed by filtered sterilization.

Methods of Use

In certain embodiments, the disclosure relates to methods of vaccination comprising administering an effective amount of the chimeric virus-like particle disclosed herein to a subject in need thereof. In certain embodiments, the disclosure relates to methods of treating or preventing a viral infection comprising administering an effective amount of the chimeric virus-like particle as disclosed herein to a subject in need thereof. In certain embodiments, the administration is intramuscular. In certain embodiments, a second administration is provided more than two weeks after an initial administration. In certain embodiments, the second administration is intranasal. In certain embodiments, the methods further comprise a third administration. In certain embodiments, the methods further comprise administration is in combination with the administration of another antiviral agent, antigen, adjuvant, or vaccine.

Other pathologic diseases and conditions are also contemplated in the context of the disclosure, especially infectious diseases associated with an infection by a pathogen such as fungi, bacteria, protozoa and viruses. Representative examples of viral pathogens include without limitation human immunodeficiency virus (e.g. HIV-1 or HIV-2), human herpes viruses (e.g. HSV1 or HSV2), cytomegalovirus, Rotavirus, Epstein Barr virus (EBV), hepatitis virus (e.g. hepatitis B virus, hepatitis A virus, hepatitis C virus and hepatitis E virus), varicella-zoster virus (VZV), paramyxoviruses, coronaviruses; respiratory syncytial virus, parainfluenza virus, measles virus, mumps virus, flaviviruses (e.g. Yellow Fever Virus, Dengue Virus, Tick-borne encephalitis virus, Japanese Encephalitis Virus), influenza virus, and typically human papilloma viruses (e.g. HPV-6, 11, 16, 18, 31. 33).

Moreover, as mentioned above, the chimeric virus-like particle, fusion protein, nucleic acid molecule, vector, infectious particle, host cell and/or composition of the present disclosure can be used as an adjuvant to enhance the immune response of an animal or human organism to a particular antigen. This particular use of the present disclosure may be made in combination with one or more transgenes or transgene products as defined above, e.g. for purposes of immunotherapy. Typically, the active agent (e.g. fusion protein, infectious particle or pharmaceutical composition of the disclosure) is administered in combination with one or more transgenes or transgene products. Accordingly, there is typically also provided a composition comprising in combination a transgene product (e.g. a viral antigen or a suicide gene product) and a fusion protein as well as a composition comprising vector(s) or viral particles encoding a transgene product and a fusion protein. The transgene and the fusion-encoding nucleic acid sequences may be expressed from the same vector or from separate vectors which may have the same origin (e.g. adenoviral vectors) or a different origin (e.g. a MVA vector encoding the particular antigen and an adenoviral vector encoding the fusion protein). The fusion protein and the transgene product (or their respective encoding vectors) can be introduced into the host cell or organism either concomitantly or sequentially either via the mucosal and/or systemic route.

Combination Therapies

In some embodiments, the disclosure relates to treating or preventing a viral infection by administering a chimeric virus-like particle in combination with a second antiviral agent. In further embodiments, a chimeric virus-like particle is administered in combination with one or more of the following agents: abacavir, acyclovir, acyclovir, adefovir, amantadine, amprenavir, ampligen, arbidol, atazanavir, atripla, boceprevir, cidofovir, combivir,darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type II, interferon type I, lamivudine, lopinavir, loviride, maraviroc, moroxydine, methisazone, nelfinavir, nevirapine, nexavir, oseltamivir (Tamiflu), peginterferon alfa-2a, penciclovir, peramivir, pleconaril, podophyllotoxin, raltegravir, ribavirin, rimantadine, ritonavir, pyramidine, saquinavir, stavudine, tenofovir, tenofovir disoproxil, tipranavir, trifluridine, trizivir, tromantadine, truvada, valaciclovir (Valtrex), valganciclovir, vicriviroc, vidarabine, viramidine zalcitabine, zanamivir (Relenza), and/or zidovudine (AZT).

Antiviral agents include, but are not limited to, protease inhibitors (PIs), integrase inhibitors, entry inhibitors (fusion inhibitors), maturation inhibitors, and reverse transcriptase inhibitors (anti-retrovirals). Combinations of antiviral agents create multiple obstacles to viral replication, i.e., to keep the number of offspring low and reduce the possibility of a superior mutation. If a mutation that conveys resistance to one of the agents being taken arises, the other agents continue to suppress reproduction of that mutation. For example, a single anti-retroviral agent has not been demonstrated to suppress an HIV infection for long. These agents are typically taken in combinations in order to have a lasting effect. As a result, the standard of care is to use combinations of anti-retrovirals.

Reverse transcribing viruses replicate using reverse transcription, i.e., the formation of DNA from an RNA template. Retroviruses often integrate the DNA produced by reverse transcription into the host genome. They are susceptible to antiviral drugs that inhibit the reverse transcriptase enzyme. In certain embodiments the disclosure relates to methods of treating viral infections by administering a chimeric virus-like particle, and a retroviral agent such as nucleoside and nucleotide reverse transcriptase inhibitors (NRTI) and/or a non-nucleoside reverse transcriptase inhibitors (NNRTI). Examples of nucleoside reverse transcriptase inhibitors include zidovudine, didanosine, zalcitabine, stavudine, lamivudine, abacavir, emtricitabine, entecavir, apricitabine. Examples of nucleotide reverse transcriptase inhibitors include tenofovir and adefovir. Examples of non-nucleoside reverse transcriptase inhibitors include efavirenz, nevirapine, delavirdine, and etravirine.

In certain embodiments, the disclosure relates to methods of treating a viral infection by administering a chimeric virus-like particle optionally with an antigen in combination with an antiviral drug, e.g., 2',3'-dideoxyinosine and a cytostatic agent, e.g., hydroxyurea.

Human immunoglobulin G (IgG) antibodies are believed to have opsonizing and neutralizing effects against certain viruses. IgG is sometimes administered to a subject diagnosed with immune thrombocytopenic purpura (ITP) secondary to a viral infection since certain viruses such as, HIV and hepatitis, cause ITP. In certain embodiments, the disclosure relates to methods of treating or preventing viral infections comprising administering a chimeric virus-like particle in combination with an immunoglobulin to a subject. IgG is typically manufactured from large pools of human plasma that are screened to reduce the risk of undesired virus transmission. The Fc and Fab functions of the IgG molecule are usually retained. Therapeutic IgGs include Privigen, Hizentra, and WinRho. WinRho is an immunoglobulin (IgG) fraction containing antibodies to the Rho(D) antigen (D antigen). The antibodies have been shown to increase platelet counts in Rho(D) positive subjects with ITP. The mechanism is thought to be due to the formation of anti-Rho(D) (anti-D)-coated RBC complexes resulting in Fc receptor blockade, thus sparing antibody-coated platelets.

EXPERIMENTAL

Construction and Expression of GPI-Anchored GIFT4

To generate a gene encoding the membrane-anchored GIFT4, the coding sequences of the signal peptide from the honeybee melittin and murine CD59 GPI anchor were fused to the 5'- and 3'-ends of the GIFT4 coding gene (derived from mouse sequences) in frame to obtain the full-length encoding gene of a GPI-anchored GIFT4 (GPI-GIFT4) by overlapping PCR. The resulting GPI-GIFT4 encoding gene was then cloned into transfer vector pFastBac-1 plasmid (Invitrogen, Carlsbad, Calif.). A recombinant baculovirus (rBV) expressing GPI-GIFT4 was generated by using the Bac-to-Bac insect cell protein expression system (Invitrogen, Carlsbad, Calif.).

To confirm whether GPI-anchored GIFT4 can be membrane-oriented translocated and expressed on cell surfaces, sf9 cells were infected with rBVs expressing GPI-GIFT4 at a MOI of 2. Two days later, cells were harvested and stained with rat anti-mouse GM-CSF antibodies (BD Biosciences) followed by PE-conjugated secondary antibodies. A non-GIFT4-related rat anti-mouse antibody was served as an antibody control. Sf9 cells infected with rBVs expressing Env were stained with anti-GM-CSF followed by PE-conjugated secondary antibodies as another control. Fluorescent intensity was recorded and analyzed by FACS with a BD FACS Canto II flow cytometer.

Production of HIV VLPs

Four different VLPs (Gag only VLPs, GIFT4/Gag VLPs, sVLPs and cVLPs) were produced for comparison using an insect cell expression system as described in Wang et al. J Virology, 2007, 81, 10869-10878. For the production of cVLPs, sf9 cells were co-infected with three rBVs respectively expressing a modified HIV Env consensus (ConS) which showed a high level of incorporation into VLPs, GPI-GIFT4, and Gag, at MOIs of 6, 2 and 3, respectively. Standard VLPs and Gag only VLPs were also produced. GIFT4/Gag VLPs were produced by co-infection of sf9 cells with rBVs expressing GPI-GIFT4 and Gag at MOIs of 2 and 3, respectively. Two days post-infection, the culture supernatant was collected and VLPs were concentrated by porous fiber filtration using the Quixstand benchtop system (GE Healthcare, Uppsala, Sweden) followed by sucrose density gradient ultracentrifugation. To quantitate the yield of purified VLPs, the protein concentration of each sample was estimated using the Bio-Rad protein assay (Bio-Rad Laboratories, Inc, Hercules, Calif.).

A diagram of the membrane-bound form of GIFT4 gene is shown in FIG. 1A. The melittin signal peptide and CD59 GPI anchoring signal-coding sequences were fused to 5' and 3'-ends of the GIFT4 encoding sequence in frame to facilitate the membrane insertion of GPI-GIFT4. Western blot (FIG. 1B) using anti-GM-CSF antibody detected a band migrating at 37 kDa in the lysate of sf9 cells infected by recombinant baculovirus (rBVs) expressing the GPI-GIFT4 gene (lane 1 in FIG. 1B), corresponding to the expected size of GPI-anchored GIFT4. The membrane anchoring of the expressed GPI-GIFT4 was further demonstrated by the enhanced fluorescent intensity measured by FACS analysis of the rBV-infected cells after cell surface staining with anti-GM-CSF antibodies, followed by PE-conjugated secondary antibodies.

VLPs were produced using the rBV expression system in insect cells. The protein composition of the resulting VLPs was characterized by western blot using antibodies specific to Gag, Env or GM-CSF. As shown in FIG. 2 (a.2), the Env incorporated into standard Env/Gag VLPs (sVLPs, lane 2) or cVLPs (lane 4) was observed to have a molecular mass of about 120 kDa. A band migrating at the expected size of GPI-GIFT4 was seen in cVLP and GIFT4/Gag VLPs (lanes 3 and 4 in a.3), demonstrating the incorporation of GPI-GIFT4 into these VLPs. The results shown in lane 4 of both a.2 and a.3 in FIG. 2 further indicate that membrane-anchored GIFT4 and Env can be co-incorporated into HIV cVLPs. To verify that the integration of GIFT4 into VLPs is through GPI anchoring on the membrane surface, FACS assay was carried out. GIFT4 was detected by the enhanced fluorescent intensity in cVLPs but not sVLPs after anti-GM-CSF antibody staining. Further, the GIFT4 signal from cVLPs was completely eliminated by treatment with PIPLC, a phosphatidylinositol-specific phospholipase which releases GPI-anchored molecules from membranes, as shown in FIG. 2*b*. Together, these data demonstrated that GIFT4 can be incorporated into VLPs, or co-incorporated into cVLPs, through GPI anchoring.

Functional Characterization of GIFT4-containing VLPs

To determine whether the anchored GIFT4 in cVLPs retains the biological activity of soluble GIFT4, whether cVLPs can induce proliferation of guinea pigs spleen cells in vitro were tested. The spleen cells were cultured in complete RPMI medium in the presence of 1μg/ml sVLPs, cVLPs, and GIFT4/Gag VLPs, respectively. Soluble GIFT4 (50 ng/ml) was used as a positive control. Following incubation at 37° C. in 5% CO2 for 2 days, the proliferation of cells was observed and imaged under an EVOS microscope (Life Technologies, Grand Island, N.Y.).

After culturing for 2 days in the presence of 1 μg/ml of cVLPs or GIFT4/Gag VLPs, was significantly higher numbers of spleen cells proliferated into colonies with larger colony sizes when compared to the control or sVLPs. Proliferation was also observed in sVLP-treated cells, although at a lower level when compared to that of the GIFT4 containing VLPs, demonstrating that VLPs themselves are also lymphocyte stimulators. These results indicate that GPI-GIFT4 incorporated into VLPs retains the biological activity of the soluble GIFT4 in stimulation of lymphocyte proliferation.

Enhanced Systemic Antibody Responses to cVLPs

To investigate whether GIFT4 incorporated into HIV VLPs enhances antibody responses against the Env immunogen, groups of guinea pigs were immunized with one intramuscular (i.m.) prime followed by two intranasal (i.n.) boosts with sVLPs, cVLPs, GIFT4/Gag VLPs or Gag only VLPs, respectively. Immune serum IgG levels specific to HIV Env at 2 weeks after each immunization were assessed by ELISA. The results shown in FIG. 3A (presented as endpoint titers) demonstrate that cVLPs induced serum antibody responses with higher titers than those observed with sVLPs ($P<0.05$). After three immunizations (bleed 3 at week 10, FIG. 3*a*), guinea pigs immunized with cVLPs exhibited 5-fold higher IgG levels than those induced by sVLPs (means of 24600 vs. 4666, $P<0.01$). These results indicated that co-incorporation of the membrane-anchored GIFT4 into VLPs is highly effective in enhancing anti-Env immune responses. Although cVLPs induced elevated IgG responses, Env-specific IgA in immune sera was not detected.

The serum IgG subclass profiles were assessed in the bleed 3 sera, and it was observed that sVLPs and cVLPs induced both IgG1 and IgG2 immune responses. The IgG2/IgG1 ratio for the sVLP group is about 9, and about 7 for the cVLP group (FIGS. 3*b* and 3*c*). Based on these data, IgG2 dominates the IgG responses to HIV VLPs. Although cVLPs induced higher IgG titers compared to sVLPs, their antibody responses show similar IgG subtype profiles. The sequence of GIFT4 used was derived from mice. Thus whether antibody responses specific to GIFT4 were induced in guinea pigs, and whether these antibodies decrease the adjuvant function of GIFT4 in subsequent immunizations as invesitgated. GIFT4-specific antibodies in immune sera was not observed.

Enhanced Mucosal Antibody Responses to cVLPs

Female Hartley strain guinea pigs were obtained from Charles River Laboratory (Wilmington, Mass.) and were separated into four groups (5 animals per group). Groups were immunized with an immunization regimen including one intramuscular (i.m.) prime followed by two intranasal (i.n.) boosts with VLP vaccines at intervals of 4 weeks. For each immunization, animals in the Gag only and GIFT4/Gag VLP groups were immunized with 100 μg total protein, respectively. Standard and cVLPs were administered using doses containing 10 μg Env, respectively. As averages, one dose of GIFT4-containing VLPs (cVLPs and GIFT4/Gag VLPs) contained about 2 μg GIFT4 calibrated by using soluble GIFT4. Two weeks after each immunization, immune sera were collected by vena cava bleeding of anesthetized guinea pigs.

Mucosal immunity is important for controlling a primary HIV-1 infection. To determine whether cVLPs induce enhanced mucosal immune responses by this immunization regimen, the secretory Env-specific IgA and IgG levels in saliva and vaginal washes were evaluated after three immunizations. As shown in FIGS. 4*a* and 4*b*, both Env-specific IgG and IgA titers in saliva samples were found to be much higher in the cVLP group than that in the sVLP group. Remarkably, at week 10, cVLP-immunized guinea pigs also showed about 5-fold higher IgG levels (FIGS. 4*c*) and 6-fold higher IgA levels (FIG. 4*d*) in vaginal washes than those induced in sVLP-immunized guinea pigs, demonstrating that the GIFT4 is an effective adjuvant for eliciting mucosal immune responses.

Enhanced Antibody Avidity

Antibody avidity for the HIV antigen is low at the early stage of infection and increases as the infection progresses while antibody matures. Neutralizing antibodies with increased avidity evolve during maturation. A significant increase in avidity has been reported after repeated antigen exposure. Several recent studies have also shown correlations between the avidity of non-neutralizing antibodies and HIV protective efficacy. Therefore, antibody avidity analysis is an effective way to evaluate antibody quality for providing protection. To determine whether cVLPs induce antibody responses to Env with enhanced avidity, six Env-pseudotyped viruses from both clades B and C, were compared. Because Env is inserted into the pseudoviral envelope, as is the case in virions. Env in pseudoviruses is functionally equal to it in viruses also, binding to target cells and mediating virus-host cell membrane fusion. Env in pseudoviruses exactly corresponds to that in viruses. Pseudotyped virus-based neutralizing assays have been extensively used to evaluate an antibody capacity for blocking HIV infection. Thus antibody avidity to pseudoviruses Env should reflect the antibody binding to HIV particles. The results shown in FIGS. 5A-B demonstrated that serum antibodies in the cVLP group showed significantly increased avidity compared to the sera from the sVLP immunized group. The cVLPs elicited antibodies with increased avidity with AIs around 40 for binding to 4 of the 6 clade B strains (FIG. 5A) as well as 4 of 6 clade C viruses (FIG. 5B) compared with sVLPs with AIs no more than 20 ($P<0.05$). Intermediate levels of avidity enhancement were found to strain 6535.3 in clade B and ZM214M.PL15 in clade C, and no change was observed with AC10.0.29 in clade B or ZM109F.PB4 (clade C) ($P>0.05$). Interestingly, although cVLPs elicited increased avidity to sVLPs as observed above, avidity to different Env among these strains compared are not significantly different.

Enhanced Antibody Neutralizing Breadth and Potency

Neutralizing antibodies can directly block viral infection by binding tightly to the functional Env, mediating virus aggregation, complement-dependent inactivation, or triggering antibody-dependent cell-mediated cytotoxicity/virus inhibition (ADCC/ADCVI), and thus are ideal targets to be elicited by a vaccine. Our results demonstrate that HIV cVLPs containing GPI-anchored GIFT4 induced higher titers of IgG compared to sVLPs. The neutralization reactivity of these antibodies was investigated using a panel of HIV clade B and C Env-pseudoviruses, the same virus panel as was used to compare antibody binding avidity in FIGS. 5A-B. As shown in FIG. 6A, serum neutralizing reactivity elicited by the cVLP group against PVO.4, a tier 3 virus which shows strong resistance to neutralization, and RHPA4259.7 (tier 2) were enhanced (approximately 30%-40% of the viruses were neutralized to lower than 20, $P<0.05$) compared to the sVLP group. Of the 6 clade C viruses tested, immune sera from cVLP group exhibited enhanced neutralization to Du156.12 (tier 2), ZM214M.PL15 (tier 2) and ZM109F.PB4 (intermediate) compared to sVLP group ($P<0.05$) (FIG. 6B). GIFT4-containing VLP and sVLP groups showed similar neutralization titers to the other viruses ($P>0.05$). These results further indicate an adjuvant effect of the membrane-anchored GIFT4 in cVLPs in inducing antibody responses with enhanced neutralizing breadth and potency.

The invention claimed is:

1. A nucleic acid encoding a fusion protein comprising the amino acid sequence of SEQ ID NO: 7.

2. A vector comprising the nucleic acid of claim 1 in operable combination with a promoter sequence.

3. An in vitro cell comprising the vector of claim 2.

4. A chimeric virus-like particle comprising the fusion protein encoded by the nucleic of claim 1.

5. The chimeric virus-like particle of claim 4, further comprising a viral envelope protein.

6. The chimeric virus-like particle of claim 5, wherein the viral envelope protein is an HIV envelope protein.

7. The chimeric virus-like particle of claim 6, wherein the viral envelope is gp160, gp120, or gp41.

8. An in vitro cell comprising the nucleic acid of claim 1.

9. A nucleic acid encoding a fusion protein comprising a variant amino acid sequence of SEQ ID NO: 7, wherein the variant comprises one conserved amino acid substitution.

10. A vector comprising the nucleic acid of claim 9 in operable combination with a promoter sequence.

11. An in vitro cell comprising the vector of claim 10.

12. A chimeric virus-like particle comprising the fusion protein encoded by the nucleic of claim 9.

13. The chimeric virus-like particle of claim 12, further comprising a viral envelope protein.

14. The chimeric virus-like particle of claim 13, wherein the viral envelope protein is an HIV envelope protein.

15. The chimeric virus-like particle of claim 14, wherein the viral envelope is gp160, gp120, or gp41.

16. An in vitro cell comprising the nucleic acid of claim 9.

* * * * *